United States Patent [19]

Kawasaki et al.

[11] Patent Number: 5,358,735
[45] Date of Patent: Oct. 25, 1994

[54] METHOD FOR MANUFACTURING SOLID OXIDE FILM AND METHOD FOR MANUFACTURING SOLID OXIDE FUEL CELL USING THE SOLID OXIDE FILM

[75] Inventors: Shinji Kawasaki, Nagoya; Shigenori Ito, Kasugai; Kiyoshi Okumura, Nagoya, all of Japan

[73] Assignee: NGK Insulators, Ltd., Japan

[21] Appl. No.: 857,965

[22] Filed: Mar. 26, 1992

[30] Foreign Application Priority Data

Mar. 28, 1991 [JP] Japan ..................... 3-87344
Jan. 31, 1992 [JP] Japan ..................... 4-16654

[51] Int. Cl.$^5$ ..................................... B05D 1/00
[52] U.S. Cl. ........................... 427/115; 427/421; 427/422; 427/426; 429/30; 429/33
[58] Field of Search ............ 427/115, 421, 422, 426; 429/30, 33

[56] References Cited

U.S. PATENT DOCUMENTS

| | | |
|---|---|---|
| 3,219,730 | 11/1965 | Bliton et al. |
| 3,481,780 | 12/1969 | Mitoff |
| 3,522,103 | 7/1970 | White et al. |
| 3,645,894 | 2/1972 | Krystyniak |
| 3,742,585 | 7/1973 | Wentzell ............ 427/422 |
| 3,753,745 | 8/1973 | Shiroyama et al. |
| 4,342,792 | 8/1982 | Brown et al. ........ 427/453 |
| 4,543,265 | 9/1985 | Kasuya ............... 427/453 |
| 4,629,537 | 12/1986 | Hsu ................. 427/115 |
| 4,895,576 | 1/1990 | Pal .................. 427/115 |
| 5,021,304 | 6/1991 | Ruka ................. 427/115 |
| 5,051,321 | 9/1991 | Kitagawa ............. 427/115 |
| 5,080,689 | 1/1992 | Pal .................. 427/115 |
| 5,085,742 | 2/1992 | Dollard .............. 427/115 |
| 5,106,654 | 4/1992 | Isenberg ............. 427/115 |
| 5,132,352 | 7/1992 | Richards ............. 427/115 |

FOREIGN PATENT DOCUMENTS

| | | |
|---|---|---|
| 0167723 | 1/1986 | European Pat. Off. |
| 1454268 | 9/1966 | France |
| 2011820 | 3/1970 | France |
| 1191315 | 5/1970 | United Kingdom |

OTHER PUBLICATIONS

Chemical Abstracts, vol. 83, No. 14, 6 Oct. 1975, Columbus, Ohio, US; abstract No. 120025x, Neuimin A. D. et al. "Plasma-torch spraying of zirconium dioxide stabilized with yttrium oxide containing iron (III) oxide and bismuth (III) oxide additions" & Tr. Inst. Elektrokhim. vol. 21, pp. 126-131.

Patent Abstracts of Japan, vol. 12, No. 385 (E-668) 14 Oct. 1988 & JP-A-63 128 566 (Mitsubishi Heavy Ind Ltd) 1 Jun. 1988.

Patent Abstracts of Japan, vol. 12, No. 153 (E-607) 11 May 1988 & JP-A-62 268 063 (Mitsubishi Heavy Ind Ltd) 20 Nov. 1987.

Patent Abstracts of Japan, vol. 14, No. 433 (E-979)(4376) 17 Sep. 1990 & JP-A-02 170 370 (Onoda Cement Co Ltd) 2 Jul. 1990.

American Ceramic Society Bulletin, vol. 42, No. 1, Jan. 1963, Columbus US, pp. 6-9, J. L. Bliton et al. "Flame Sprayed Zirconia Films for Fuel Cell Components", p. 7, right column, line 32-p. 8, left column, line 2.

*Primary Examiner*—Shrive Beck
*Assistant Examiner*—Vi Duong Dang
*Attorney, Agent, or Firm*—Parkhurst, Wendel & Rossi

[57] ABSTRACT

A first method for manufacturing a solid oxide film having a highly densified solid oxide film having a small thickness and an improved electric conductivity; and a second method for manufacturing a solid oxide fuel cell in which a solid oxide film formed on an air electrode or a fuel electrode is manufactured by the first method. The solid oxide fuel cell according to the present invention is capable of generating a high power. The solid oxide film is formed on a substrate in such manner that a solid oxide material is sprayed on the substrate to form a sprayed solid oxide film thereon; Then a solution of metal compound including at least one metal selected from a group of manganese, iron, cobalt, nickel, copper and zinc is impregnated into the sprayed solid oxide film; and the sprayed solid oxide film is subjected to a heat treatment in order to increase an airtightness of the film. It may be possible to use a material for spraying, in which 1~10 parts by weight of an oxide of said metal is contained, instead of the impregnation, or to obtain a material for spraying by mixing the compound powder containing the metal and the solid oxide material in a spray gun via separately arranged powder supply devices.

38 Claims, 2 Drawing Sheets

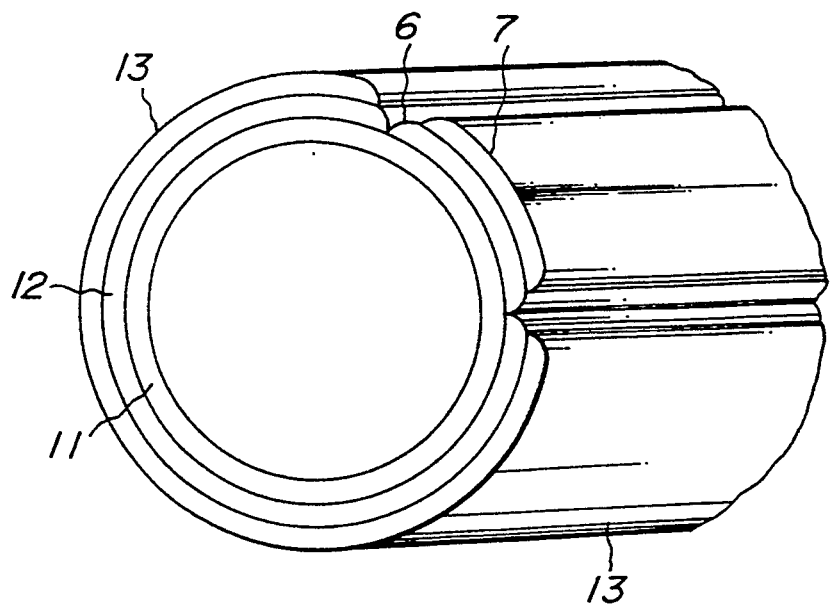
FIG._2
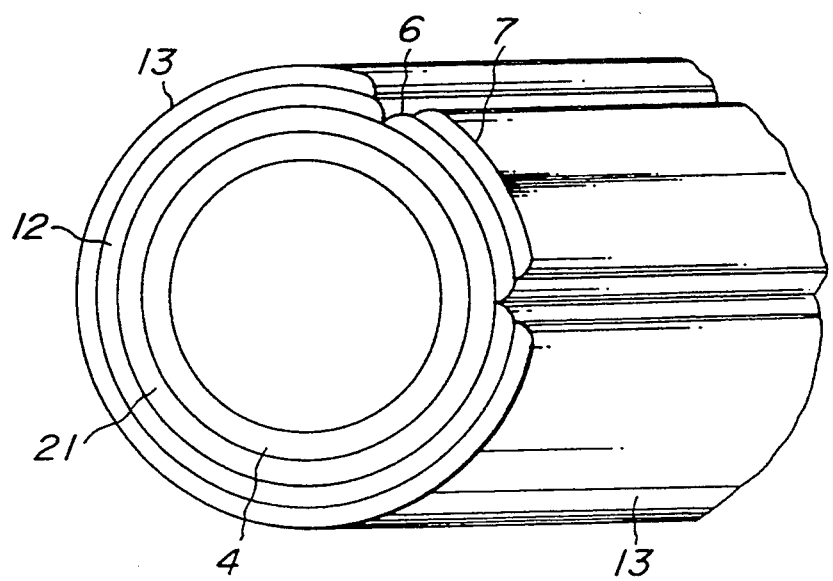
FIG._3

METHOD FOR MANUFACTURING SOLID OXIDE FILM AND METHOD FOR MANUFACTURING SOLID OXIDE FUEL CELL USING THE SOLID OXIDE FILM

BACKGROUND OF THE INVENTION

1. Field of the Invention

The present invention relates to a method for manufacturing a solid oxide film and a method for manufacturing a solid oxide fuel cell using the solid oxide film.

2. Related Art Statement

Recently, fuel cells have been recognized as a viable power generating source. The fuel cell is capable of directly converting chemical energy possessed by fuel to electric energy. Since the fuel cell is free from the limitation of Carnot's cycle, the fuel cell essentially has a high energy conversion efficiency. Further, various fuels such as naphtha, natural gas, methanol, coal reformed gas and heavy oil may be used, additionally, these fuels may be used with a low pollutant level. Moreover, the power generating efficiency of fuel cells is not influenced by the scale of the equipment. Therefore, power generation with the aid of fuel cells is an extremely promising technique.

Particularly, since the solid oxide fuel cell (hereinafter abbreviated as SOFC) operates at a high temperature of 1000° C. or more, the reaction of electrodes thereof is very active and the use of a noble metal catalyst such as expensive platinum is not required. In addition, since the SOFC has a low polarization and a relatively high output voltage, the energy conversion efficiency is considerably higher than that of other fuel cells. Furthermore, since the SOFC is constructed with solid materials, it is stable in structure and has a long service life.

In such SOFC, it is desired to make the solid oxide film as this as possible. However, in a chemical vapor deposition method or an electrochemical vapor deposition method, which are conventional methods for manufacturing the solid oxide thin film, there are drawbacks that an apparatus for manufacturing the solid oxide film becomes large, an area on which the solid oxide film can be formed is small and a processing speed for forming the film is slow. Therefore, the cost for manufacturing the film becomes high and it is difficult to obtain a large area solid oxide film. Additionally, in case of the electrochemical vapor deposition method, the shape of the substrate is limited to be cylindrical.

For instance, it has been known; (ref. Sunshine Journal 1981, Vol. 2, No. 1 pps 32-35) how to manufacture a solid oxide fuel cell with the aid of plasma spray coating; and the plasma spray coating is excellent in that a thin solid oxide film with a high density can be formed quickly in an easy manner.

Further, in Japanese Preliminarily Patent Publication Nos. 61-198569 and 61-195570, it is known that is a spray substance, in which cerium oxide or zirconium oxide and metal oxide such as alkaline-earth metals or rare-earth element are soluted, is sprayed on a substrate with the aid of the plasma spray coating after the particle size of the material is adjusted, it forms a solid oxide film on the substrate.

However, airtightness of the film formed by the plasma spray coating is generally low. Therefore, when a solid oxide film of the solid oxide fuel cell is formed by the plasma spray coating, the airtightness of the film is not sufficient. Therefore, when operating such SOFC, hydrogen, mono carbonate oxide, etc. is leaked through the solid oxide film. Then, the electromotive force per one SOFC becomes smaller than 1 V, and the output thereof is decreased, so that the energy converting efficiency from fuel to electric power is aggravated.

In this case, it is considered to make the solid oxide film thick to prevent the leakage of fuel, However, a diffused resistor for an ion diffusion in a bulk becomes so large that a resistor of the cell becomes large. Therefore, it is strongly desired to develop a technique to improve the power output of the unit SOFC by making the solid oxide film thin and making the density of the film high so that fuel leakage is not generated.

SUMMARY OF THE INVENTION

The present invention has for its first purpose to provide a method for manufacturing a solid oxide film by which the solid oxide film can be formed with a thin thickness, a high density and an improved electric conductivity.

The present invention has for its second purpose to provide a method for manufacturing solid oxide fuel cell being applied the thin and highly densified solid oxide film thereto to obtain a solid oxide fuel cell having a high power output.

According to the first aspect of the present invention, a method for manufacturing a solid oxide film comprises the following steps:

preparing a solid oxide material;

spraying said solid oxide material on a substrate to form a sprayed solid oxide film;

impregnating a solution of a compound containing at least one kind of metal selected from a group of manganese, iron, cobalt, nickel, copper and zinc into said sprayed solid oxide film; and subjecting the solid oxide film to a heat treatment in order to improve airtightness of the solid oxide film formed on the substrate.

According to the second aspect of the present invention, a method for manufacturing a solid oxide fuel cell comprises the following steps of:

preparing a solid oxide material;

spraying said solid oxide material on an air electrode to form a sprayed solid oxide film on the air electrode;

impregnating a solution of a compound containing at least one kind of metal selected from a group of manganese, iron, cobalt, nickel, copper and zinc into said solid oxide film formed on the air electrode;

subjecting the sprayed solid oxide film to a heat treatment in order to improve airtightness of the solid oxide film; and providing a fuel electrode film on a surface of the solid oxide film formed on the air electrode.

According to the third aspect of the present invention, a method for manufacturing a solid oxide fuel cell comprises the following steps of:

preparing a solid oxide material;

spraying said solid oxide material on a fuel electrode to form a sprayed solid oxide film on the fuel electrode;

impregnating a solution of a compound containing at least one kind of metal selected from a group of manganese, iron, cobalt, nickel, copper and zinc into said solid oxide film formed on the fuel electrode;

subjecting the sprayed solid oxide film to a heat treatment in order to improve airtightness of the solid oxide film formed on the fuel electrode; and providing an air electrode film on a surface of the solid oxide film formed on the fuel electrode.

According to the fourth aspect of the present invention, a method for manufacturing a solid oxide film comprises the following steps:

preparing a solid oxide material for spraying containing 1~10 parts by weight in total of an oxide of at least one kind of metal selected from a group of manganese, iron, cobalt, nickel, copper and zinc with respect to 100 parts by weight of solid oxide raw material;

spraying the thus prepared solid oxide material on a substrate to form a solid oxide film thereon;

subjecting the thus formed solid oxide film to a heat treatment in order to improve airtightness of the solid oxide film formed on the substrate.

According to the fifth aspect of the present invention, a method for manufacturing a solid oxide fuel cell comprises the following steps:

preparing a solid oxide material for spraying containing 1~10 parts by weight in total of an oxide of at least one kind of metal selected from a group of manganese, iron, cobalt, nickel, copper and zinc with respect to 100 parts by weight of solid oxide raw material;

spraying the thus prepared solid oxide material on an air electrode to form a solid oxide film thereon;

subjecting the solid oxide film formed on the air electrode to a heat treatment in order to improve airtightness of the solid oxide film; and providing a fuel electrode on a surface of the solid oxide film formed on the air electrode.

According to the sixth aspect of the present invention, a method for manufacturing a solid oxide fuel cell comprises the following steps:

preparing a solid oxide material for spraying containing 1~10 parts by weight in total of an oxide of at least one kind of metal selected from a group of manganese, iron, cobalt, nickel, copper and zinc with respect to 100 parts by weight of solid oxide raw material;

spraying the thus prepared solid oxide material on a fuel electrode to form a solid oxide film thereon;

subjecting the solid oxide film formed on the fuel electrode to a heat treatment in order to improve airtightness of the solid oxide film; and providing an air electrode on a surface of the solid oxide film formed on the fuel electrode.

According to the seventh aspect of the present invention, a method for manufacturing a solid oxide film comprises the following steps:

preparing a powder of compound containing at least one metal selected from a group of manganese, iron, cobalt, nickel, copper and zinc;

preparing a solid oxide raw material;

supplying the compound and the solid oxide raw material to a spray gun via individually arranged powder supply devices;

melting the compound and the raw material in the spray gun;

spraying the melted compound and raw material on a substrate to form a sprayed solid oxide film thereon;

subjecting the thus formed sprayed solid oxide film to a heat treatment in order to improve airtightness of the solid oxide film formed on the substrate.

According to the eighth aspect of the present invention, a method for manufacturing a solid oxide fuel cell comprises the following steps:

preparing a powder of compound containing at least one metal selected from a group of manganese, iron, cobalt, nickel, copper and zinc;

preparing a solid oxide raw material;

supplying the compound and the solid oxide raw material to a spray gun via individually arranged powder supply devices;

melting the compound and the material in the spraying gun;

spraying the melted compound and raw material on an air electrode to form a sprayed solid oxide film on the air electrode;

subjecting the solid oxide film formed on the air electrode to a heat treatment in order to improve airtightness of the solid oxide film; and providing a fuel electrode on the solid oxide film formed on the air electrode.

According to the ninth aspect of the present invention, a method for manufacturing a solid oxide fuel cell comprises the following steps:

preparing a powder of compound containing at least one metal selected from a group of manganese, iron, cobalt, nickel, copper and zinc;

preparing a solid oxide raw material;

supplying the compound and the solid oxide material to a spray gun via individually arranged powder supply devices;

melting the compound and the raw material in the spray gun;

spraying the melted compound and raw material on a fuel electrode to form a sprayed solid oxide film on the fuel electrode;

subjecting the solid oxide film formed on the fuel electrode to a heat treatment in order to improve airtightness of the solid oxide film; and providing an air electrode on the solid oxide film formed on the air electrode.

It should be noted that the meaning of "spraying on a substrate" includes the case of spraying the material on a surface of the substrate and the case of spraying the solid oxide material on a surface of other films, such as an air electrode film and a fuel electrode film, formed on the surface of substrate; further the meaning of "spraying the solid oxide material on an air electrode or (on a fuel electrode )" includes the case of spraying the solid oxide material on the surface of the air electrode film or (fuel electrode film) formed on a surface of the porous substrate and the case of spraying the solid oxide material on a surface of an air electrode substrate made by an air electrode material or (on a surface of a fuel electrode substrate made by a fuel electrode material ), respectively.

According to the present invention, since the sprayed solid oxide film is subjected to the heat treatment, the airtightness of the solid oxide film is improved. Therefore, there are no fine cracks or fine defects, which are peculiarly caused in the process of the plasma spraying, and the structure of the solid oxide film is densified in an even manner. Further, since a solution of a compound containing at least one kind of metal selected from the group of manganese, iron, cobalt, nickel, copper and zinc is impregnated into the sprayed solid oxide film, when subjecting the solid oxide film to a heat treatment, the densification of the structure of the sprayed solid oxide film is elevated, the required heat treatment temperature is reduced and the required heat treatment time is reduced. It should be noted that the same effects can be obtained in the case that an oxide of at least one kind of metal selected from the group of manganese, iron, cobalt, nickel, copper and zinc is preliminarily included in the raw material for spraying and then the material is sprayed on the substrate and subjected to the heat treatment.

Further, it may be possible to arrange such that the compound powder containing at least one kind of metal selected from a group of manganese, iron, cobalt, nickel, copper and zinc and a solid oxide material is supplied to the spray gun via individually arranged powder supply means and then the powder and the material are melted in the spray gun. In this case, the abovementioned metal is distributed in the sprayed solid oxide film as a whole in an even manner; and thus the densification of the structure of the sprayed solid oxide film is elevated much more when the sprayed solid film is subjected to the heat treatment.

As described in the above, according to the invention, it is possible to obtain the solid oxide film having the same airtightness and the same electric conductivity as the conventional solid oxide film, which is manufactured by electrochemical vapor deposition, etc., by applying very easy techniques, such as spraying, impregnation and heat treatment. Therefore, the apparatus for manufacturing the solid oxide film can be made compact in size, and cheap in cost therefor, and further, the film is grown at a high speed and a large size solid oxide film having a high airtightness can be obtained easily.

Thus, the solid oxide film manufactured by the method of the invention can be suitably used as a solid oxide film for use as an oxygen sensor and a device for measuring oxygen concentration. Further, since the solid oxide film manufactured by the method of the invention has high airtightness, it can be used as a non-oxidizable film for coating a metal member.

Furthermore, since a thin solid oxide film having high airtightness and a high electric conductivity can be obtained according to the invention, when use is made of a solid oxide film of a solid oxide fuel cell, the internal resistance of the cell becomes small and the power thereof becomes high.

Furthermore, in comparison of the method of the invention with the conventional method, i.e. electrochemical vapor deposition, for manufacturing a solid oxide film, the technique of the present invention is much easier than the conventional method, and only simple devices such as a general spraying device and an electric furnace for the heat treatment are required to grow the film; thus the manufacturing cost for the film becomes lower.

Moreover, by the conventional method, i.e. electrochemical vapor deposition, manufacturing a comparatively small-sized cylindrical solid oxide fuel cell is possible, but, it is difficult to manufacture a plate-like solid oxide fuel cell. In contrast to this, the present invention can be applied for manufacturing both the cylindrical solid oxide fuel cell and the plate-like solid oxide fuel cell. Additionally, the present invention can easily be applied for manufacturing not only the prolonged cylindrical cell and the plate-like cell having a large area but also a collecting cell having a complex shape.

A mixture or a solid solution consisting of an alkali-earth metal or rare-earth metal and a cirium oxide or zirconium oxide is preferably used as the solid oxide material. In case that at least one kind of metal selected from a group of manganese, iron, cobalt, nickel copper and zinc is contained in the solid oxide material for spraying, a compound (for example, oxide) of the above mentioned metal or metals is added to a powder of said mixture or said solid solution, and then the compound and the powder are mixed to obtain a mixed powder; and the thus obtained mixed powder is preliminarily sintered to solute the metal component or components into the material for spraying. The metal component or components serve to make the required heat treatment temperature low and the required heat treatment time short.

Then, the solid oxide material for spraying obtained in such a manner is sprayed on a substrate to form a sprayed solid oxide film on the substrate. Spraying is conducted with the aid of plasma spraying method. It should be noted that the plasma spraying under a lower pressure is much more effective than the plasma spraying under a normal pressure. But, even if the plasma spraying is conducted under the normal pressure, the solid oxide film would have enough airtightness by the heat treatment conducted thereafter.

As the other method for manufacturing the solid oxide film, spraying the solid oxide material on a substrate; impregnating a solution of compound containing at least one kind of said metals into the film; drying the film; and then conducting a heat treatment with the film. In this case, acetates, nitrates, sulfates, and salts of organic acids of said metals are preferably used as the compound. Further, it may be possible to impregnate the solution not only into the solid oxide film but also the film and substrate. Furthermore, in order to impregnate the solution at least into the film, it is preferred to immerse the sprayed solid oxide film, and the film and substrate as demanded, into the solution.

In the case that a compound powder containing at least one kind of metal selected from a group of manganese, iron, cobalt, nickel, copper and zinc and a solid oxide material is melted in a spray gun, oxide, carbonate or hydroxide of the metal or metals is preferably used as the compound. In this case, the compound powder and the solid oxide material are supplied to the spray gun via separately arranged powder supply devices. Therefore, it may be possible to make a gradient in a composition of the sprayed solid oxide film by varying the supplied amounts of the compound powder and the solid oxide material as time is passed and as occasion demands.

In the case of spraying a solid oxide material mainly consisting of zirconium oxide on the surface of an air electrode, an insulating layer consisting of $La_2Zr_2O_7$, etc. may be produced between the solid oxide film and the air electrode at the step of the heat treatment conducted thereafter. However, by the existence of manganese or cobalt in the sprayed solid oxide film in accordance with the invention, such insulating layer would not be produced.

BRIEF DESCRIPTION OF THE DRAWINGS

FIG. 2 is a partial perspective view illustrating a cylindrical SOFC; and

FIG. 3 is a partial perspective view indicating another cylindrical SOFC.

Figure 1:
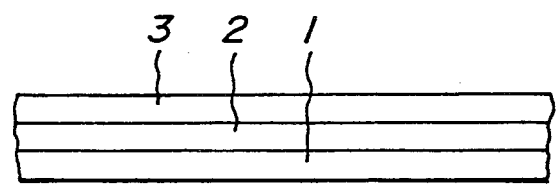
FIG. 1 is a partial front view showing a plate-like SOFC.

In the example shown in FIG. 1, a solid oxide film 2 is formed on a surface of a plate-like air electrode substrate 1, made of an air electrode material, and on a surface of the solid oxide film is arranged a fuel electrode 3. It may be possible to arrange the layers such that the solid oxide film is formed on a surface of a plate-like fuel electrode substrate, which is made by a fuel electrode material, and further arrange an air electrode on the surface of the solid oxide film.

In the example depicted in FIG. 2, a solid oxide film 12 is provided on a surface of a cylindrical air electrode substrate 11 made of an air electrode material; and on a surface of the solid oxide film 12 is arranged a fuel electrode film 13. There is arranged an interconnector 6 on the air electrode substrate 11 in a right upper region in FIG. 2; Additionally a connecting terminal 7 is arranged on the interconnector 6. A plurality of cylindrical SOFCs are connected to each other in series by connecting the air electrode substrate 11 of the SOFC and the fuel electrode film 13 of a contiguously arranged SOFC via the interconnector 6 and the connecting terminal 7, These cylindrical SOFCs are connected to each other in parallel by connecting the fuel electrode films 13 to each other by means of a metal felt such as Ni felt. Contrary to the configuration, it may be possible to arrange the solid oxide film on a cylindrical fuel electrode substrate made of a fuel electrode material and to arrange the air electrode film on the surface of the solid oxide film.

In the SOFC illustrated in FIG. 3, an air electrode film 21 is formed around an outer circumference of a cylindrical substrate 4 made of a porous ceramic, and a solid oxide film 12 and fuel electrode film 13 are arranged around the outer circumference of the air electrode film 21 in this order. The other construction is the same as the SOFC depicted in FIG. 2, and the explanation therefor is omitted. It may be also possible to exchange the arrangement of the air electrode film 21 and the fuel electrode film 13.

The air electrode may be produced by a doped or non-doped oxide such as $LaMnO_3$, $CaMnO_3$, $LaNiO_3$, $LaCoO_3$ and $LaCrO_3$; but strontium-doped or calcium-doped $LaMnO_3$ is preferred. These doped or non-doped $LaMnO_3$, $CaMnO_3$, $LaNiO_3$, $LaCoO_3$, $LaCrO_3$ are not limited to an oxide having a definite composition but an oxide having a nondefinite composition such as La lacking composition and Ca lacking composition can be used. The oxide having a non-definite composition effects to limit the production of $La_2Zr_2O_7$. And fuel electrode made of Nickel-Zirconia cermet or Cobalt-Zirconia cermet is preferably used. A gas including a fuel such as hydrogen, reformed hydrogen, carbon monoxide and hydrocarbon is used as a fuel gas and a gas including an oxidizing agent such as oxygen, hydrogen peroxide, etc. is used as an oxidized gas.

DETAILED EXPLANATION OF THE PREFERRED EMBODIMENTS

Embodiment 1

Eight mol. % of $Y_2O_3$ stabilized zirconia powder were molded under a molding pressure of 200 kg/cm$^2$ to obtain circular plates having a diameter of 70 mm and thickness of 3 mm. The plate was sintered for five hours at a temperature of 1450° C. and then processed to obtain a circular plate-like substrates having diameters of 50 mm, thicknesses of 1 mm and porosities of 23%. Eight mol. of $Y_2O_3$ stabilized zirconia (8YSZ) powder were prepared as the solid oxide material; and the powder was sprayed on the substrates with the aid of the plasma spraying to form films of 8YSZ thereon with thicknesses of 500 μm. Then the substrates were ground off by buffing to obtain only the sprayed solid oxide films. Twenty grams of manganese acetate were soluted in eighty grams of water; and the sprayed solid oxide film was immersed therein; then the manganese acetate was impregnated into the solid oxide films by degassing in a vacuum. Then, the solid oxide films were dried at a temperature of 100° C. The impregnation and drying were repeated to obtain sprayed solid oxide films which are different in the number of time of impregnation. The heat treatment was conducted on the thus obtained Mn impregnated sprayed solid oxide films and non-impregnated sprayed solid oxide films except the comparative example, respectively, at a temperature of 1300°~1450° C. for three hours. A permeation amount of $N_2$ gas was measured after conducting the heat treatment concerning each the sprayed solid oxide film. The measurement results are shown in Table 1.

TABLE 1

| | Thickness of sprayed film (μm) | Number of times of impregnation | Heat treatment temperature (°C.) | Permeation amount of $N_2$ (cc · min$^{-1}$ · cm$^{-2}$) |
|---|---|---|---|---|
| Comparative sample | 500 | non | non | 3 |
| Reference sample | 500 | non | 1450 | 0.09 |
| Present invention | 500 | 1 | 1450 | 0.001 |
| Present invention | 500 | 2 | 1350 | 0.02 |
| Present invention | 500 | 10 | 1300 | 0.1 |
| Present invention | 500 | 2 | 1300 | 0.4 |

In the same manner, but with the solution of compound for impregnation was altered by iron acetate, nickel nitrate, cobalt acetate, copper sulfate or zinc acetate, the experiment was conducted. Each solid oxide film was subjected to a heat treatment after the impregnation was conducted two times. Then the permeation amount of $N_2$ gas through each film was measured in the same manner. The experimental results are shown in Table 2.

TABLE 2

| | Thickness of sprayed film (μm) | Impregnation liquid | Heat treatment temperature (°C.) | Permeation amount of $N_2$ (cc · min$^{-1}$ · cm$^{-2}$) |
|---|---|---|---|---|
| Present invention | 500 | iron acetate | 1400 | 0.003 |
| Present invention | 500 | nickel nitrate | 1400 | 0.009 |
| Present invention | 500 | cobalt acetate | 1400 | 0.006 |
| Present invention | 500 | copper sulfate | 1400 | 0.003 |
| Present invention | 500 | zinc acetate | 1400 | 0.003 |

Embodiment 2

The following is an embodiment of the method for manufacturing a solid oxide fuel cell according to the present invention.

Lanthanum manganite powder was molded under a molding pressure of 200 kg/cm$^2$ to obtain bodies each having a diameter of 50 mm and thickness of 3 mm and then the bodies were sintered at a temperature of 1450° C. for five hours. The sintered bodies were processed to obtain air electrode substrates each having a diameter of 30 mm, thickness of 1 mm and porosity of 25%. Eight mol % of $Y_2O_3$ stabilized zirconia (8YSZ) powder was prepared and the powder was sprayed on the air electrode substrates by plasma spraying to form an 8 YSZ layer having a thickness of 200/μm on each substrate. Then the laminated bodies were immersed into a solution of 20 g of manganese acetate and 80 g of water at normal temperature; The bodies were then degassed in vacuum in order to impregnate the bodies with the manganese acetate. Thereafter, the laminated bodies were dried at a temperature of 100° C. The impregnation and drying processes were repeated to obtain several kinds of the laminated bodies, to which the impregnation and drying were applied a different number of times. The thus obtained laminated bodies containing manganese and layered bodies containing no manganese were subjected to a heat treatment at a predetermined temperature for three hours. It should be noted that no heat treatment was conducted on a comparative sample. Further, nickel zirconia paste was applied on the surface of the solid oxide films formed on the air electrode substrates with the aid of screen printing and then the bodies were sintered at a temperature of 1200° C. for three hours to form a fuel electrode on each solid oxide film. On the air electrodes of the thus obtained unit solid oxide fuel cells, was fed oxygen gas and on the fuel electrodes thereof, was fed $H_2+H_2O$ to measure open circuit voltages OCV of the unit cells. Further, the resistances of the unit cells were measured by a cole-cole-plot. Furthermore, an existence of $La_2Zr_2O_7$ layer was recognized by SEM (reflected image of an electron) of a polished cross-section of the laminated body. The measurement results are shown in Table 3.

impregnation of manganese. In comparison the solid oxide fuel cell according to the present invention with the reference solid oxide fuel cell, when the cell is manufactured under the condition that the heat treatment temperature is considerably low, the open circuit voltage of the cell becomes close to the theorical value 1.11 V, because of the impregnation of manganese.

Embodiment 3

Eight mol % of $Y_2O_3$ stabilized zirconia powder was molded under a molding pressure of 200 kg/cm² to obtain circular plate-like molding bodies each having diameter of 50 mm and thickness of 3 mm. The bodies were sintered at a temperature of 1450° C. for five hours and then the sintered bodies were processed to obtain substrates for spraying each having a diameter of 30 mm, a thickness of 1 mm and a porosity of 25%. Eight mol % of $Y_2O_3$ stabilized zirconia (8YSZ) powder were prepared as a solid oxide raw material and 0.5 parts by weight, 1 part by weight, 5 parts by weight or 10 parts by weight of the metal oxides shown in Table 4 were added with respect to 100 parts by weight of the 8YSZ powder. Then into the thus obtained metal oxide mixed powders were added 1 kg of water and then mixed with the aid of an attritor to obtain slurries. The slurries were grained into fine grains having a mean diameter of 30 μm, by a spray dryer and then the fine grains were preliminarily sintered at a temperature of 1200° C. for three hours. The sintered grains were put through a sieve of 44 μm mesh to obtain raw material powders for spraying. The thus obtained raw material powders for

TABLE 3

|  | Thickness of sprayed film (μm) | Number of times of immersion | Heat treatment temperature (°C.) | Open circuit voltage OCV | Resistant (Ω · cm²) | $La_2Zr_2O_7$ layer |
| --- | --- | --- | --- | --- | --- | --- |
| Comparative sample | 200 | non | non | 0.89 | 1.0 | non |
| Reference sample | 100 | non | 1400 | 1.00 | 0.9 | exist |
| Reference sample | 100 | non | 1500 | 1.11 | 1.2 | exist |
| Present invention | 200 | 1 | 1500 | 1.11 | 0.4 | little |
| Present invention | 200 | 1 | 1400 | 1.11 | 0.3 | non |
| Present invention | 200 | 10 | 1300 | 1.11 | 0.2 | non |
| Present invention | 50 | 1 | 1300 | 1.05 | 0.08 | non |
| Present invention | 100 | 1 | 1300 | 1.08 | 0.1 | non |
| Present invention | 200 | 1 | 1300 | 1.09 | 0.2 | non |

As clear from the embodiments 1 and 2, it is possible to make airtight the sprayed solid oxide layer, according to the present invention. Additionally, in case the solid oxide film is applied to the solid oxide fuel cell, the open circuit voltage of the cell is improved by a combination of the impregnation of manganese and the heat treatment. Further the resistance of the cell can be made remarkably small because an $La_2ZrO_3$ having an insulating property is not generated or generated slightly when subjecting the cell to the heat treatment due to the spraying were sprayed on the surfaces of said substrates by plasma spraying to laminate the 8YSZ layer of 200 μm or 500 μm. Thereafter, the substrates were ground off to take out only the sprayed solid oxide films. The thus taken out films were subjected to a heat treatment at temperatures shown in the Table 4 for five hours, respectively and then $N_2$ gas transmitting coefficients were measured concerning each example. The measurement results are shown in Table 4.

TABLE 4

|  | Thickness of sprayed film (μm) | Additive | Adding amount | Heat treatment temperature (°C.) | Permeation coefficient of $N_2$ (cm⁴ · g⁻¹ · s⁻¹) |
| --- | --- | --- | --- | --- | --- |
| Comparative sample | 500 | non | non | non | $5 \times 10^{-5}$ |
| Reference | 500 | non | non | 1450 | $8 \times 10^{-6}$ |

TABLE 4-continued

| | Thickness of sprayed film (μm) | Additive | Adding amount | Heat treatment temperature (°C.) | Permeation coefficient of $N_2$ $(cm^4 \cdot g^{-1} \cdot S^{-1})$ |
|---|---|---|---|---|---|
| sample Reference sample | 500 | $MnO_2$ | 0.5 | 1450 | $7 \times 10^{-6}$ |
| Present invention | 500 | $MnO_2$ | 1 | 1450 | $3 \times 10^{-9}$ |
| Present invention | 500 | $Fe_2O_3$ | 5 | 1350 | $4 \times 10^{-8}$ |
| Present invention | 500 | $Fe_2O_3$ | 5 | 1300 | $7 \times 10^{-7}$ |
| Present invention | 200 | NiO | 10 | 1350 | $7 \times 10^{-8}$ |

Embodiment 4

The following is another embodiment of a method for manufacturing a solid oxide fuel cell according to the present invention.

Lanthanum manganite powder was molded under a molding pressure of 200 kg/cm² to obtain circular plate-like molded bodies having a diameter of 50 mm and thickness of 3 mm. The molded bodies were sintered at a temperature of 1450° C. for five hours and then the sintered bodies were processed to obtain air electrode substrates having diameters of 30 mm, thicknesses of 1 mm and porosities of 25%. Eight mol % of $Y_2O_3$ stabilized zirconia (8YSZ) powder (electrofused zirconia) were prepared as a material for spraying. A predetermined amount of metal oxides shown in the following Table 4 were added into the material, respectively, and each material and each of the metal oxides were mixed with each other in a pot mill with organic gravel for four hours. The mixed materials were sintered at a temperature of 1300° C. for five hours and then were put through a sieve of 149 μm mesh to obtain a plurality of kinds of material powders for spraying. The thus obtained material powders for spraying were sprayed on the surfaces of the air electrode substrates, respectively, to form a laminate layer of 8YSZ having a predetermined thickness on each substrate. The thus obtained sprayed solid oxide films were subjected to heat treatments at temperatures shown in the Table 5. Further, a nickel zirconia paste was applied on the surfaces of the solid oxide films by means of screen printing, and then the films were sintered at a temperature of 1200° C. for three hours to form fuel electrode films on the solid oxide film. On the air electrodes of the thus obtained single solid oxide fuel cells, was fed an oxygen gas and on the fuel electrodes thereof, was fed $H_2+H_2O$ to measure an open circuit voltage OCV under a temperature of 1000° C. Further, the resistance of the unit cells were measured by a cole-cole-plot. The measurement results are shown in Table 5.

TABLE 5

| | Thickness of sprayed film (μm) | Additive | Adding amount | Heat treatment temperature (°C.) | Open circuit voltage OCV | Resistance $(\Omega \cdot cm^2)$ |
|---|---|---|---|---|---|---|
| Comparative sample | 200 | non | non | non | 0.89 | 1.2 |
| Reference sample | 100 | non | non | 1550 | 1.00 | 0.9 |
| Reference sample | 100 | non | non | 1600 | 1.11 | 1.2 |
| Present invention | 200 | $MnO_2$ | 1 | 1500 | 1.11 | 0.4 |
| Present invention | 200 | $MnO_2$ | 1 | 1400 | 1.11 | 0.5 |
| Present invention | 200 | CoO | 10 | 1300 | 1.08 | 0.3 |
| Present invention | 50 | CuO | 1 | 1300 | 1.05 | 0.1 |
| Present invention | 100 | ZnO | 1 | 1300 | 1.08 | 0.2 |
| Present invention | 200 | ZnO | 1 | 1300 | 1.09 | 0.3 |
| Comparative sample | 200 | $MnO_2$ | 12 | non | 0.85 | 0.9 |
| Reference sample | 100 | CuO | 11 | 1400 | 0.88 | 0.7 |

As apparent from the above explained embodiments 3 and 4, by adding a specific metal oxide into the material for spraying and subjecting the sprayed solid oxide fuel films to a heat treatment, the open circuit voltage of the solid oxide fuel cell becomes the theoretical value of 1.11 V or becomes close thereto, and the resistance of the cell becomes very small, in comparison with the solid oxide fuel cells of the comparative sample, which were manufactured without being subjected to the heat treatment. Further, comparing the solid oxide fuel cells manufactured by the method according to the present invention with the reference solid oxide fuel cells, the resistances of the cells according to the invention is lower than the reference samples and the voltages at the open circuits are higher than those of the reference samples regardless of the lower heat treatment temperature. The reason why the resistance of the cells of the present invention becomes lower by adding the specific metal oxides is that the $La_2Zr_2O_7$ is not produced or only a little $La_2Zr_2O_7$ is produced while the cells are subjected to the heat treatment. Further, when adding the amount of specific metal oxide exceeds over 10 parts by weight, the voltage at the open circuits decreases and the resistance of the unit cell becomes high. On the contrary, when the added amount of specific metal oxide is less than 1 part by weight, the sprayed solid oxide film is not densified so much, and then the permeation coefficient of $N_2$ does not become small, and the effect to reduce the generation of the insulating material of $La_2Zr_2O_7$ can not be obtained sufficiently.

Embodiment 5

Eight mol % of $Y_2O_3$ stabilized zirconia powder was molded at a molding pressure of 200 kg/cm$_2$ to obtain molded circular plate-like bodies having diameters of 50 mm and thicknesses of 3 mm. The molded bodies were sintered at a temperature of 1450° C. for five hours and then processed to obtain circular substrates for spraying having diameters of 30 mm, thicknesses of 1 mm and porosities of 25%. Eight mol % of $Y_2O_3$ stabilized zirconia powder and metal oxides shown in Table 6 were prepared as a material for spraying. The 8YSZ powder and each metal oxide powder were fed to a spray gun via the separately arranged powder supply devices, respectively, and melted in the spray gun. The melted materials were sprayed on the surfaces of the substrates for spraying with the aid of plasma spraying to obtain a plurality of kinds of solid oxide films. The thicknesses of the sprayed layers were 200 μm or 500 μm. Then, the substrates for spraying were ground off to take out only sprayed solid oxide films. The thus obtained solid oxide films were subjected to heat treatments at the temperatures shown in Table 6 for five hours and then the permeation coefficients of $N_2$ gas concerning the respective films were measured. The measurement results are shown in Table 6. It should be noted that in the item of "adding amount" in Table 6 the supply amount of each metal oxide powder is indicated by using a unit of part by weight with respect to the supply amount of 100 parts by weight of 8YSZ powder.

Embodiment 6

The following is another embodiment for manufacturing a solid oxide fuel cell in which the solid oxide film is formed by the method according to the fifth embodiment explained above.

Lanthanum manganite powder was molded at a molding pressure of 200 kg/cm$^2$ to obtain circular plate-like molded bodies having diameters of 50 mm and thicknesses of 3 mm. These bodies were sintered at a temperature of 1450° C. for five hours and then processed to obtain air electrode substrates having diameters of 30 mm, thicknesses of 1 mm and porosities of 25%, respectively. Eight mol % of $Y_2O_3$ stabilized zirconia (8YSZ) powder (electrofused zirconia) and metal oxide powders shown in Table 7 were prepared as a material for spraying. These 8YSZ powder and each metal oxide powder were fed to a spray gun via the separately arranged powder supply devices and melted in the spray gun to get a plurality of kinds of melted material. The melted materials were sprayed on the surfaces of the air electrode substrates by means of plasma spraying to obtain sprayed films having thicknesses shown in Table 7 on the substrates. Then these sprayed solid oxide films were subjected to heat treatments at temperatures shown in Table 7. Further, a nickel zirconia paste was applied on the respective solid oxide films by means of screen printing, and the paste applied films with nickel zirconia paste were sintered at a temperature of 1200° C. for three hours to obtain fuel electrode films on the solid oxide film. Oxygen gas was supplied onto the air electrodes and $H_2+H_2O$ onto the fuel electrodes and then voltages at the open circuit OCV of the respective cells were measured at a temperature of 1000° C. Further, resistances of the respective cells were measured by a cole cole plot. These measurement results are shown in Table 7. It should be noted, in adding amount" in Table 7, the supply amount of metal oxide is indicated by using a unit part by weight with respect to when the supply amount of 100 parts by weight of 8YSZ powder.

TABLE 6

| | Thickness of sprayed film (μm) | Metal oxide | Adding amount | Heat treatment temperature (°C.) | Permeation coefficient of $N_2$ (cm$^4 \cdot$ g$^{-1} \cdot$ S$^{-1}$) |
|---|---|---|---|---|---|
| Comparative sample | 500 | non | non | non | $5 \times 10^{-5}$ |
| Reference sample | 500 | non | non | 1450 | $8 \times 10^{-6}$ |
| Present sample | 500 | $MnO_2$ | 0.5 | 1450 | $1 \times 10^{-6}$ |
| Present invention | 500 | $MnO_2$ | 1 | 1450 | $2 \times 10^{-9}$ |
| Present invention | 500 | $Fe_2O_3$ | 5 | 1350 | $1 \times 10^{-8}$ |
| Present invention | 500 | $Fe_2O_3$ | 5 | 1300 | $8 \times 10^{-7}$ |
| Present invention | 200 | NiO | 10 | 1350 | $9 \times 10^{-8}$ |

TABLE 7

| | Thickness of sprayed film (μm) | Metal oxide | Adding amount | Heat treatment temperature (°C.) | Open circuit voltage OCV | Resistance (Ω · cm$^2$) |
|---|---|---|---|---|---|---|
| Comparative sample | 200 | non | non | non | 0.89 | 1.2 |
| Reference sample | 100 | non | non | 1550 | 1.00 | 0.9 |
| Reference sample | 100 | non | non | 1600 | 1.11 | 1.2 |

TABLE 7-continued

| | Thickness of sprayed film (μm) | Metal oxide | Adding amount | Heat treatment temperature (°C.) | Open circuit voltage OCV | Resistance ($\Omega \cdot cm^2$) |
|---|---|---|---|---|---|---|
| Present invention | 200 | $MnO_2$ | 1 | 1500 | 1.11 | 0.3 |
| Present invention | 200 | $MnO_2$ | 1 | 1400 | 1.11 | 0.4 |
| Present invention | 200 | CoO | 10 | 1300 | 1.08 | 0.4 |
| Present invention | 50 | CuO | 1 | 1300 | 1.04 | 0.2 |
| Present invention | 100 | ZnO | 1 | 1300 | 1.09 | 0.2 |
| Present invention | 200 | ZnO | 1 | 1300 | 1.10 | 0.4 |
| Comparative sample | 200 | $MnO_2$ | 12 | non | 0.87 | 0.9 |
| Present sample | 100 | CuO | 11 | 1400 | 1.00 | 0.6 |

As apparent from the above embodiments, when the solid oxide material and metal oxide powder were fed into the spray gun via the separately arranged powder supply devices and then the melted materials were subjected to the heat treatment, the same effect as those of the first to fourth embodiments can be obtained.

As explained in detail in the above, according to the invention, it is possible to solve the drawbacks of fine cracks or defects, which are generated in the solid oxide film manufactured with the aid of plasma spraying, and possible to obtain a solid oxide film having a high density and even structure. Further, by impregnating a specified metal into the sprayed solid oxide film by the method mentioned in the above, the structure of the film is further densified when the sprayed solid oxide film is subjected to a heat treatment. Therefore, it is possible to make the required heat treatment temperature low and the required heat treatment time short. In such manner, according to the invention, the solid oxide film having the same airtightness and the same electric conductivity as those of the conventional solid oxide film having a high airtightness manufactured by an EVD method, etc. can be obtained with the aid of very easy techniques such as spraying, impregnation and heat treatment. Therefore, the equipment for manufacturing the solid oxide film can be made compact, the cost therefor kept low, the speed for film growth high, and a highly densified solid oxide film having a large area can be obtained easily.

What is claimed is:

1. A method for manufacturing a solid oxide electrolyte film for a fuel cell comprising the following steps:
   preparing a solid oxide electrolyte material;
   spraying said solid oxide electrolyte material on a substrate to form a sprayed solid oxide film;
   impregnating a solution of a compound comprising at least one metal selected from the group consisting of manganese, cobalt, nickel, copper and zinc into said sprayed solid oxide electrolyte film; and
   subjecting the solid oxide electrolyte film to a heat treatment after the impregnation step in order to improve an airtightness of the solid oxide electrolyte film formed on the substrate.

2. A method for manufacturing a solid oxide electrolyte film according to claim 1, wherein:
   said solid oxide electrolyte material is a mixture or a solid solution consisting of (i) cerium oxide and alkali-earth metal or rare-earth metal or (ii) zirconium oxide and alkali-earth metal or rare-earth metal.

3. The method of claim 1, wherein said solid oxide electrolyte material is plasma sprayed on said substrate.

4. A method for manufacturing a solid oxide fuel cell comprising the following steps:
   preparing a solid oxide material;
   spraying said solid oxide material on an air electrode to form a sprayed solid oxide film on the air electrode;
   impregnating a solution of a compound comprising at least one metal selected from the group consisting of manganese, cobalt, nickel, copper and zinc into said solid oxide film formed on the air electrode;
   subjecting the sprayed solid oxide film to a heat treatment after the impregnation step in order to improve an airtightness of the slid oxide film; and
   providing a fuel electrode film on a surface of the solid oxide film formed on the air electrode.

5. A method for manufacturing a solid oxide fuel cell according to claim 4, wherein:
   said air electrode is formed by doped or non-doped $LaMnO_3$, $CaMnO_3$, $LaNiO_3$, $LaCoO_3$ or $LaCrO_3$.

6. A method for manufacturing a solid oxide fuel cell according to claim 5, wherein:
   said doped or non-doped $LaMnO_3$, $CaMnO_3$, $LaNiO_3$, $LaCoO_3$ or $LaCrO_3$ has a specified structure.

7. A method for manufacturing a solid oxide fuel cell according to claim 5, wherein:
   said doped or non-doped $LaMnO_3$, $CaMnO_3$, $LaNiO_3$, $LaCoO_3$ or $LaCrO_3$ has a non-specified structure.

8. The method of claim 4, wherein said solid oxide material is plasma sprayed on said air electrode.

9. A method for manufacturing a solid oxide fuel cell comprising the following steps:
   preparing a solid oxide material;
   spraying said solid oxide material on a fuel electrode to form a sprayed solid oxide film on the fuel electrode;
   impregnating a solution of a compound comprising at least one metal selected from the group consisting of manganese, cobalt, nickel, copper and zinc into said solid oxide film formed on the fuel electrode;
   subjecting the sprayed solid oxide film to a heat treatment after the impregnation step in order to improve an airtightness of the solid oxide film formed on the fuel electrode; and providing an air electrode film on a surface of the solid oxide film formed on the fuel electrode.

10. A method for manufacturing a solid oxide fuel cell according to claim 9, wherein:
said air electrode is formed by doped or non-doped $LaMnO_3$, $CaMnO_3$, $LaNiO_3$, $LaCoO_3$ or $LaCrO_3$.

11. A method for manufacturing a solid oxide fuel cell according to claim 10, wherein:
said doped or non-doped $LaMnO_3$, $CaMnO_3$, $LaNiO_3$, $LaCoO_3$ or $LaCrO_3$ has a specified structure.

12. A method for manufacturing a solid oxide fuel cell according to claim 10, wherein:
said doped or non-doped $LaMnO_3$, $CaMnO_3$, $LaNiO_3$, $LaCoO_3$ or $LaCrO_3$ has a non-specified structure.

13. The method of claim 9, wherein said solid oxide material is plasma sprayed on said fuel electrode.

14. A method for manufacturing a solid oxide electrolyte film for a fuel cell comprising the following steps:
preparing a solid oxide electrolyte material for spraying containing 1~10 parts by weight in total of an oxide of at least one metal selected from the group consisting of manganese, cobalt, copper and zinc, with respect to 100 parts by weight of solid oxide electrolyte raw material;
spraying the thus prepared solid oxide electrolyte material on a substrate to form a solid oxide electrolyte film on the substrate;
subjecting the thus formed solid oxide electrolyte film to a heat treatment in order to improve an airtightness of the solid oxide electrolyte film formed on the substrate.

15. The method of claim 14, wherein said solid oxide electrolyte material is plasma sprayed on said substrate.

16. A method for manufacturing a solid oxide fuel cell comprising the following steps:
preparing a solid oxide material for spraying containing 1~10 parts by weight in total of an oxide of at least one metal selected from the group consisting of manganese, cobalt, nickel, copper and zinc, with respect to 100 parts by weight of solid oxide raw material;
spraying the thus prepared solid oxide material on an air electrode of to form a solid oxide film on the air electrode;
subjecting the solid oxide film formed on the air electrode to a heat treatment in order to improve an airtightness of the solid oxide film; and
providing a fuel electrode on a surface of the solid oxide film formed on the air electrode.

17. A method for manufacturing a solid oxide fuel cell according to claim 16, wherein:
said air electrode if formed by doped or non-doped $LaMnO_3$, $CaMnO_3$, $LaNiO_3$, $LaCoO_3$ or $LaCrO_3$.

18. A method for manufacturing a solid oxide fuel cell according to claim 17, wherein:
said doped or non-doped $LaMnO_3$, $CaMnO_3$, $LaNiO_3$, $LaCoO_3$ or $LaCrO_3$ has a specified structure.

19. A method for manufacturing a solid oxide fuel cell according to claim 17, wherein:
said doped or non-doped $LaMnO_3$, $CaMnO_3$, $LaNiO_3$, $LaCoO_3$ or $LaCrO_3$ has a non-specified structure.

20. The method of claim 16, wherein said solid oxide material is plasma sprayed on said air electrode.

21. A method for manufacturing a solid oxide fuel cell comprising the following steps:
preparing a solid oxide material for spraying containing 1~10 parts by weight in total of an oxide of at least one kind of metal selected from a group of manganese, cobalt, copper and zinc with respect to 100 parts by weight of solid oxide raw material;
spraying the thus prepared solid oxide material on a fuel electrode to form a solid oxide film on the fuel electrode;
subjecting the solid oxide film formed on the fuel electrode to a heat treatment in order to improve an airtightness of the solid oxide film; and
providing an air electrode on a surface of the solid oxide film formed on the fuel electrode.

22. A method for manufacturing a solid oxide fuel cell according to claim 21, wherein:
said air electrode is formed by doped or non-doped $LaMnO_3$, $CaMnO_3$, $LaNiO_3$, $LaCoO_3$ or $LaCrO_3$.

23. A method for manufacturing a solid oxide fuel cell according to claim 22, wherein:
said doped or non-doped $LaMnO_3$, $CaMnO_3$, $LaNiO_3$, $LaCoO_3$ or $LaCrO_3$ has a specified structure.

24. A method for manufacturing a solid oxide fuel cell according to claim 22 wherein:
said doped or non-doped $LaMnO_3$, $CaMnO_3$, $LaNiO_3$, $LaCoO_3$ or $LaCrO_3$ has a non-specified structure.

25. The method of claim 21, wherein said solid oxide material is plasma sprayed on said fuel electrode.

26. A method for manufacturing a solid oxide electrolyte film for a fuel cell comprising the following steps:
preparing a powder of a compound containing at least one metal selected from the group consisting of manganese, cobalt, nickel, copper and zinc;
preparing a solid oxide electrolyte raw material;
supplying the compound and the solid oxide electrolyte raw material to a spray gun via individually arranged powder supply devices;
melting the compound and the solid oxide electrolyte raw material in the spray gun;
spraying the melted compound and solid oxide electrolyte raw material on a substrate to form a sprayed solid oxide electrolyte film thereon;
subjecting the thus formed sprayed solid oxide electrolyte film to a heat treatment in order to improve and airtightness of the solid oxide electrolyte film formed on the substrate.

27. A method for manufacturing a solid oxide electrolyte film according to claim 26, wherein:
said compound powder is metal oxide, carbonate or hydroxide of one of said metals.

28. The method of claim 26, wherein said melted compound and solid oxide electrolyte raw material are plasma sprayed on said substrate.

29. A method for manufacturing a solid oxide fuel cell comprising the following steps:
preparing a powder of compound containing at least one metal selected from the group consisting of manganese, cobalt, nickel, copper and zinc;
preparing a solid oxide raw material;
supplying the compound and the solid oxide raw material to a spray gun via individually arranged powder supply devices;
melting the compound and the solid oxide raw material in the spraying gun;

spraying the melted compound and solid oxide raw material on an air electrode to form a sprayed solid oxide film on the air electrode;

subjecting the solid oxide film formed on the air electrode to a heat treatment in order to improve an airtightness of the solid oxide film; and providing a fuel electrode on the solid oxide film formed on the air electrode.

30. A method for manufacturing a solid oxide fuel cell according to claim 29, wherein:

said air electrode is formed by doped or non-doped $LaMnO_3$, $CaMnO_3$, $LaNiO_3$, $LaCoO_3$ or $LaCrO_3$.

31. A method for manufacturing a solid oxide fuel cell according to claim 30, wherein:

said doped or non-doped $LaMnO_3$, $CaMnO_3$, $LaNiO_3$, $LaCoO_3$ or $LaCrO_3$ has a specified structure.

32. A method for manufacturing a solid oxide fuel cell according to claim 30, wherein:

said doped or non-doped $LaMnO_3$, $CaMnO_3$, $LaNiO_3$, $LaCoO_3$ or $LaCrO_3$ has a non-specified structure.

33. The method of claim 29, wherein said melted compound and solid oxide raw material are plasma sprayed on said air electrode.

34. A method for manufacturing a solid oxide fuel cell comprising the following steps:

preparing a powder of compound containing at least one metal selected from the group consisting of manganese, cobalt, nickel, copper and zinc;

preparing a solid oxide raw material supplying the compound and the solid oxide raw material to a spray gun via individually arranged powder supply devices;

melting the compound and the solid oxide raw material in the spray gun;

spraying the melted compound and solid oxide raw material on a fuel electrode to form a sprayed solid oxide film on the fuel electrode;

subjecting the solid oxide film formed on the fuel electrode to a heat treatment in order to improve the airtightness of the solid oxide film; and providing an air electrode on the solid oxide film formed on the fuel electrode.

35. A method for manufacturing a solid oxide fuel cell according to claim 34, wherein:

said air electrode is formed by doped or non-doped $LaMnO_3$, $CaMnO_3$, $LaNiO_3$, $LaCoO_3$ or $LaCrO_3$.

36. A method for manufacturing a solid oxide fuel cell according to claim 35, wherein:

said doped or non-doped $LaMnO_3$, $CaMnO_3$, $LaNiO_3$, $LaCoO_3$ or $LaCrO_3$ has a specified structure.

37. A method for manufacturing a solid oxide fuel cell according to claim 33, wherein:

said doped or non-doped $LaMnO_3$, $CaMnO_3$, $LaNiO_3$, $LaCoO_3$ or $LaCrO_3$ has a non-specified structure.

38. The method of claim 34, wherein said melted compound and solid oxide raw material are plasma sprayed on said fuel electrode.

* * * * *